US006187560B1

(12) United States Patent
Beeley et al.

(10) Patent No.: US 6,187,560 B1
(45) Date of Patent: Feb. 13, 2001

(54) POLYNUCLEOTIDES AND POLYPEPTIDES BELONGING TO THE UNCOUPLING PROTEINS FAMILY

(75) Inventors: Lee James Beeley, Dorking; Kelly Paine, Warminster; Robert James Godden, Whitehaven, all of (GB)

(73) Assignee: SmithKline Beecham plc (GB)

( * ) Notice: Under 35 U.S.C. 154(b), the term of this patent shall be extended for 0 days.

(21) Appl. No.: 09/142,565

(22) PCT Filed: Mar. 2, 1998

(86) PCT No.: PCT/GB98/00633

§ 371 Date: Jun. 30, 1999

§ 102(e) Date: Jun. 30, 1999

(87) PCT Pub. No.: WO98/39432

PCT Pub. Date: Sep. 11, 1998

(30) Foreign Application Priority Data

Mar. 5, 1997 (GB) ................................................ 9704551
Mar. 18, 1997 (GB) ................................................ 9705614
Jul. 16, 1997 (EP) ................................................ 97305305

(51) Int. Cl.[7] ............................. C12P 21/06; C07H 17/00
(52) U.S. Cl. ..................... 435/69.1; 435/325; 435/252.3; 435/320.1; 536/23.1
(58) Field of Search .......................... 536/23.1; 435/325, 435/320.1, 252.3, 69.1

(56) References Cited

PUBLICATIONS

L. Hillier, et al., "Homo Sapiens clone 628529 similar to uncoupling protein", Jan. 21, 1997, XP002067896, Accession No. AA192136.

O. Boss et al., "Uncoupling protein–3: a new member of the mitochondrial carrier family with tissue–specific Expression", May 12, 1997, FEBS Letters 408, pp. 39–42.

Copy of International Search Report (PCT/GB98/00633) mailed Jul. 3, 1998.

Cinti et al. "Immunohistochemical Localization of Leptin and Uncoupling Protein in White and Brown Adipose Tissue", Endocrinology, vol. 138(2) pp. 797–804 (1997).

Cassard et al. "Human Uncoupling Protein Gene: Structure, Comparison With Rat Gene, and Assignment To the Long Arm of Chromosome 4" Journal of Cellular Biochemistry, vol. 43(3) pp. 255–264 (1990).

Chengjun et al. "Leptin Is a Metabolic Gate for the Onset of Puberty in the Female Rat" The Endocrinology Journal, vol. 138(2) pp. 855–858 (1997).

Fleury et al. "Uncoupling protein–2: a novel gene linked to obesity and hyperinsulinemia" Nature Genetics vol. 15 pp. 269–272 (1997).

Vidal–Puig et al. "UCP3 An Uncoupling Protein Homologue Expressed Preferentially and Abundantly in Skeletal Muscle and Brown Adipose Tissue." Biochem Biophys Res Comm, vol. 235(1) pp. 79–82 (1997).

GenBank Accession No. U69135.
GenBank Accession No. U76367.
Hillier et al. GI1781960, Jan. 1997.*
Boss et al. #A, GI:2183020, Jan. 1997.*
Boss et al. #B, GI:2183020, Jan. 1997.*
Boss et al. #C, 2GI:183017, Dec. 1996.*
Boss et al. #D, GI:2183017, Dec. 1996.*

* cited by examiner

Primary Examiner—Karen Cochrane Carlson
(74) Attorney, Agent, or Firm—William T. Han; Ratner & Prestia; William T. King

(57) ABSTRACT

HNFCW60 polypeptides and polynucleotides and methods for producing such polypeptides by recombinant techniques are disclosed. Also disclosed are methods for utilizing HNFCW60 polypeptides and polynucleotides in the design of protocols for the treatment of obesity, diabetes, hyperlipademia and body weight disorder, among others, and diagnostic assays for such conditions.

12 Claims, 4 Drawing Sheets

FIGURE 1. Nucleotide and translated Amino Acid sequence from HNFCW60 (SEQ ID NOS: 1 and 2, respectively.)

```
  1  CGCCCGGGCAGGTCAAGGAGGGGCCATCCAATCCCTGCTGCCACCTCC    48

49  TGGGATGGAGCCCTAGGGAGCCCCTGTGCTGCCCCTGCCGTGGCAGGA    96

97  CTCACAGCCCCACCGCTGCACTGAAGCCCAGGGCTGTGGAGCAGCCTC   144

145  TCTCCTTGGACCTCCTCTCGGCCCTAAAGGGACTGGGCAGAGCCTTCC   192

193  AGGACTATGGTTGGACTGAAGCCTTCAGACGTGCCTCCCACCATGGCT   240
              M  V  G  L  K  P  S  D  V  P  P  T  M  A

241  GTGAAGTTCCTGGGGGCAGGCACAGCAGCCTGTTTTGCTGACCTCGTT   288
      V  K  F  L  G  A  G  T  A  A  C  F  A  D  L  V

289  ACCTTTCCACTGGACACAGCCAAGGTCCGCCTGCAGATCCAGGGGGAG   336
      T  F  P  L  D  T  A  K  V  R  L  Q  I  Q  G  E

337  AACCAGGCGGTCCAGACGGCCCGGCTCGTGCAGTACCGTGGCGTGCTG   384
      N  Q  A  V  Q  T  A  R  L  V  Q  Y  R  G  V  L

385  GGCACCATCCTGACCATGGTGCGGACTGAGGGTCCCTGCAGCCCCTAC   432
      G  T  I  L  T  M  V  R  T  E  G  P  C  S  P  Y

433  AATGGGCTGGTGGCCGGCCTGCAGCGCCAGATGAGCTTCGCCTCCATC   480
      N  G  L  V  A  G  L  Q  R  Q  M  S  F  A  S  I

481  CGCATCGGCCTCTACGACTCCGTCAAGCAGGTGTACACCCCCAAAGGC   528
      R  I  G  L  Y  D  S  V  K  Q  V  Y  T  P  K  G

529  GCGGACAACTCCAGCCTCACTACCCGGATTTTGGCCGGCTGCACCACA   576
      A  D  N  S  S  L  T  T  R  I  L  A  G  C  T  T

577  GGAGCCATGGCGGTGACCTGTGCCCAGCCCACAGATGTGGTGAAGGTC   624
      G  A  M  A  V  T  C  A  Q  P  T  D  V  V  K  V

625  CGATTTCAGGCCAGCATACACCTCGGGCCATCCAGGAGCGACAGAAAA   672
      R  F  Q  A  S  I  H  L  G  P  S  R  S  D  R  K

673  TACAGCGGGACTATGGACGCCTACAGAACCATCGCCAGGGAGGAAGGA   720
      Y  S  G  T  M  D  A  Y  R  T  I  A  R  E  E  G
```

FIGURE 1A. Nucleotide and translated Amino Acid sequence from HNFCW60 (SEQ ID NOS: 1 and 2, respectively.)

```
721   GTCAGGGGCCTGTGGAAAGGAACTTTGCCCAACATCATGAGGAATGCT    768
      V  R  G  L  W  K  G  T  L  P  N  I  M  R  N  A

769   ATCGTCAACTGTGCTGAGGTGGTGACCTACGACATCCTCAAGGAGAAG    816
      I  V  N  C  A  E  V  V  T  Y  D  I  L  K  E  K

817   CTGCTGGACTACCACCTGCTCACTGACAACTTCCCCTGCCACTTTGTC    864
      L  L  D  Y  H  L  L  T  D  N  F  P  C  H  F  V

865   TCTGCCTTTGGAGCCGGCTTCTGTGCCACAGTGGTGGCCTCCCCGGTG    912
      S  A  F  G  A  G  F  C  A  T  V  V  A  S  P  V

913   GACGTGGTGAAGACCCGGTATATGAACTCACCTCCAGGCCAGTACTTC    960
      D  V  V  K  T  R  Y  M  N  S  P  P  G  Q  Y  F

961   AGCCCCCTCGACTGTATGATAAAGATGGTGGCCCAGGAGGGCCCCACA    1008
      S  P  L  D  C  M  I  K  M  V  A  Q  E  G  P  T

1009  GCCTTCTACAAGGGATTTACACCCTCCTTTTTGCGTTTGGGATCCTGG    1056
      A  F  Y  K  G  F  T  P  S  F  L  R  L  G  S  W

1057  AACGTGGTGATGTTCGTAACCTATGAGCAGCTGAAACGGGCCCTGATG    1104
      N  V  V  M  F  V  T  Y  E  Q  L  K  R  A  L  M

1105  AAAGTCCAGATGTTACGGGAATCACCGTTTTGAACAAGACAAGAAGGC    1152
      K  V  Q  M  L  R  E  S  P  F  *

1153  CACTGGTAGCTAACGTGTCCGAAACCAGTTAAGAATGGAAG    1193
```

FIGURE 2. Nucleotide and Amino Acid sequence from a HNFCW60 (SEQ ID NOS: 3 and 4, respectively.)

```
  1  CTGGACTACCACCTGCTCACTGACAACTTCCCCTGCCACTTTGTCTCTGCCTTTGGAGCC   60
     L   D   Y   H   L   L   T   D   N   F   P   C   H   F   V   S   A   F   G   A

61  GGCTTCTGTGCCACAGTGGTGGCCTCCCCGGTGGACGTGGTGAAGACCCGGTATATGAAC  120
     G   F   C   A   T   V   V   A   S   P   V   D   V   V   K   T   R   Y   M   N

121  TCACCTCCAGGCCAGTACTTCAGCCCCCTCGACTGTATGATAAAGATGGTGGCCCAGGAG  180
     S   P   P   G   Q   Y   F   S   P   L   D   C   M   I   K   M   V   A   Q   E

181  GGCCCACAGgCCTTCTACAAGGGGTGAGCCTCCTCCTGCCTCC  223
     G   P   Q   A   F   Y   K   G   *   A   S   S   C   L
```

FIGURE 3. Nucleotide and partially translated Amino Acid sequence from HNFCW60 (SEQ ID NOS: 5 and 6, respectively.)

SEQ ID NO: 5

```
  1   AAGAGCTCAX XXTXTATGTT GAATXATTTT TTTTXXTGGC TGCAGCTGGG
 51   TCTCCAGGAA GCXTATTTAA ATTTXAACAG CTATTGCAGA TCACCCTCCA
101   AATGTGGCCA AATGAACACA AGTGGGCCTC TXTTTXCTXT XTXTCTXAGG
151   AXAACATGGA TAATCTGAGA XTTGTTAACC CTAGAAAGGA AAATXTGGAA
201   TCTXCTCAGC TGGGGTGGGA TCCTCTGGCT GAGACCATTG GAATGGGGCA
251   CTATGGCCCC AAAACTGGGG CCTGTGGCCT TGCAGCCAGG GCATCCATTT
301   TTXCCATTTC CCATTCCTCC CTCCCCAYCS ATWKGRMAKS MMKSMSTCAS
351   SGGCYTSYKG AACAGGAACT TTSCCCAACA TCATGXAGGA ATGCTATCGT
401   CAACTGTSCT GAGGTGGTGA CCTACGACAT CCTCAAGGAG AAGCTGCTGG
451   ACTAYCACCT GCTCACTGAC AACTTCCCCT GCCACTTTGT CTCTGCCTTT
501   GGAGCCGGCT TCTGTGCCAC AGTGGTGGCM TCCCCGGTGG ACGTGGTGAA
551   GACCCGGTAT ATGAACTCAC CTCCAGGCCA GTACTTCAGC CCCCTCGACT
601   GTATGATAAA GATGGTGGCC CAGGAGSGCC ACACAGCCTT CTACAAGGGA
651   KTKASMCTCC TCCTKYYTSC AGYWYKSSMT CCYAGAGAAC AGKGGCTKMT
701   GTTCKTWWCS WATGAGCAGC TGAAACGGGC CCTGATGAAA GTCCAGATGT
751   TACGGGAATC ACCGTTTTGA ACAAGACAAG AAGGCCACTG GTAGCTAACG
801   TGTCCGAAAC CAGTTAAGAA TGGAAGAAAA CGGTGCATCC ACGXACACAT
851   GGACACAGAC CCACACATXT T
```

SEQ ID NO: 6

Sequence numbers refer to equivalent positions of nucleotides in HNFCW60

```
375  GTXPNIMRNAIVNCXEVVTYDILKEKLLDYHLLTDNFPCHFVSAFGAGFCATVVASPVDV  524
525  VKTRYMNSPPGQYFSPLDCMIKMVAQEXHTAFYKG  650
```

POLYNUCLEOTIDES AND POLYPEPTIDES BELONGING TO THE UNCOUPLING PROTEINS FAMILY

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to the Uncoupling proteins family, hereinafter referred to as HNFCW60. The invention also relates to inhibiting or activating the action of such polynucleotides and polypeptides.

BACKGROUND OF THE INVENTION

Uncoupling protein is a peptide that is believed to be located in the mitochondria of mammalian brown adipose tissue (BAT) and, more recently, in other tissues such as murine muscle (MUCP2, Ricquier et al., Genbank accessionnumber:U69135). It is predominant in rodent fat deposits (Saverio et al., The Endocrinology Journal, 138 (2), 1997), and leads to a dissipation of the proton gradient across the inner membrane of the mitochondrion. This, in turn, uncouples the oxidative phosphorylation chain, and "decontrols" the process. The roles played by uncoupling protein (UCP) are that of an important factor in the thermogenesis of tissue, and of energy expenditure as a whole. Therefore, this could be used to combat obesity and body weight -associated disorder by increasing BAT oxidation.

Human UCP is found predominantly in brown adipocytes (Cassard et al., Journal of Cell Biochemistry, 43, 1990). UCP mRNA is expressed at a higher rate when β-3 adrenoreceptors are agonized by, for example BRL 37344 (Chengjun et al., The Endocrinology Journal, 138(2), 1997), which suggests a use for the protein in controlling insulin dependent diabetes. Patent application no WO96/05861 disloses a gene sequence with high homology to MUCP2. Human UCP2 is described by Fleury et al. in Nature Genetics, 1997, 15, 269. More recently, a further member of the family, Uncoupling protein-3, has been described (Boss O et al., FEBS Lett, May 12, 1997, 408(1), 39–42; Vidal-Puig A et al., Biochem Biophys Rs Commun, Jun. 9, 1997, 235(1), 79–82). These papers were however published after the two priority dates (Mar. 5, 1997 and Mar. 18, 1997) claimed in the present application.

There is a need for identification and characterization of further members of the Uncoupling proteins family which can play a role in preventing, ameliorating or correcting dysfunction or diseases, including, but not limited to, obesity, diabetes, hyperlipidaemia and body weight disorder.

SUMMARY OF THE INVENTION

In one aspect, the invention relates to HNFCW60 polypeptides and recombinant materials and methods for their production. Another aspect of the invention relates to methods for using such HNFCW60 polypeptides and polynucleotides. Such uses include the treatment of obesity, diabetes, hyperlipidaemia and body weight disorder, among others. In still another aspect, the invention relates to methods to identify agonists and antagonists using the materials provided by the invention, and treating conditions associated with HNFCW60 imbalance with the identified compounds. Yet another aspect of the invention relates to diagnostic assays for detecting diseases associated with inappropriate HNFCW60 activity or levels.

BRIEF DESCRIPTION OF THE DRAWINGS

FIGS. 1 and 1A shows the nucleotide and deduced amino acid sequence from HNFCW60 (SEQ ID NOS: 1 and 2);

FIG. 2 shows the nucleotide and deduced amino acid sequence from HNFCW60 (SEQ ID NOS: 1 and 2);

FIG. 3 shows the nucleotide and deduced amino acid sequence from HNFCW60 (SEQ ID NOS: 1 and 2);

DESCRIPTION OF THE INVENTION

Polypeptides of the Invention

The present invention relates to HNFCW60 polypeptides and their uses. Novel polypeptides include the polypeptide of SEQ ID NO:2 and isolated polypeptides encoded by a polynucleotide comprising the nucleotide sequence contained in SEQ ID NO:1. In further aspects relating to uses, HNFCW60 polypeptides include polypeptides which have at least 70, 80, 90, 95, 97–99% or 100% identity with the polypeptide of SEQ ID NO:2.

The HNFCW60 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Biologically active fragments of the HNFCW60 polypeptides are also included in the invention. A fragment is a polypeptide having an amino acid sequence that entirely is the same as part, but not all, of the amino acid sequence of the aforementioned HNFCW60 polypeptides. As with HNFCW60 polypeptides, fragments may be "freestanding," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of HNFCW60 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of HNFCW60 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Biologically active fragments are those that mediate HNFCW60 activity, including those with a similar activity or an improved activity, or with a decreased undesirable activity. Also included are those that are antigenic or immunogenic in an animal, especially in a human.

Preferably, all of these polypeptide fragments retain the biological activity of the HNFCW60, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The HNFCW60 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

The present invention also relates to HNFCW60 polynucleotides and their uses. Novel polynucleotides include a polynucleotide comprising the nucleotide sequence contained in SEQ ID NO:1 encoding the polypeptide of SEQ ID NO:2, as well as the polynucleotide of SEQ ID NO:1. In further aspects relating to uses, HNFCW60 polynucleotides include polynucleotides which have at least 70, 80, 90, 95, 97–99% or 100% identity with the polynucleotide of SEQ ID NO:1.

The invention also provides polynucleotides which are complementary to such HNFCW60 polynucleotides.

HNFCW60 of the invention is structurally related to other proteins of the Uncoupling protein family, as shown by the results of sequencing the cDNA encoding human HNFCW60. The cDNA sequence contains an open reading frame (199 to 1135) encoding a polypeptide of 312 amino acids. The nucleotide sequence of SEQ ID NO:1 has one conservative base difference where a C at position 495 is a T in position 480/450 for the Boss and Vidal-Puig (vide infra) published sequences, respectively. The polypeptide sequence of SEQ ID NO:2 is identical to that of Boss and Vidal-Puig.

The present invention also relates to partial or other polynucleotide and polypeptide sequences which were first identified prior to the determination of the corresponding full length sequences of SEQ ID NO:1 and SEQ ID NO:2.

Accordingly, in a further aspect, polynucleotides of the present invention include an isolated polynucleotide comprising:

(a) a nucleotide sequence which has at least 70% identity, preferably at least 80% identity, more preferably at least 90% identity, yet more preferably at least 95% identity, even more preferably at least 97–99% identity to SEQ ID NO:3 or SEQ ID NO:5 over the entire length of SEQ ID NO:3 or SEQ ID NO:5, respectively;

(b) a nucleotide sequence which has at least 70% identity, preferably at least 80% identity, more preferably at least 90% identity, yet more preferably at least 95% identity, even more preferably at least 97–99% identity, to SEQ ID NO:3 or SEQ ID NO:5 over the entire length of SEQ ID NO:3 or SEQ ID NO:5, respectively;

(c) the polynucleotide of SEQ ID NO:3 or SEQ ID NO:5; or (d) a nucleotide sequence encoding a polypeptide which has at least 70% identity, preferably at least 80% identity, more preferably at least 90% identity, yet more preferably at least 95% identity, even more preferably at least 97–99% identity, to the amino acid sequence of SEQ ID NO:4 or SEQ ID NO:6 over the entire length of SEQ ID NO:4 or SEQ ID NO:6, respectively;

as well as the polynucleotide of SEQ ID NO:3 or SEQ ID NO:5.

Polypeptides of the present invention further include a polypeptide which:

(a) comprises an amino acid sequence which has at least 70% identity, preferably at least 80% identity, more preferably at least 90% identity, yet more preferably at least 95% identity, most preferably at least 97–99% identity, to that of SEQ ID NO:4 or SEQ ID NO:6 over the entire length of SEQ ID NO:4 or SEQ ID NO:6, respectively;

(b) has an amino acid sequence which is at least 70% identity, preferably at least 80% identity, more preferably at least 90% identity, yet more preferably at least 95% identity, most preferably at least 97–99% identity, to the amino acid sequence of SEQ ID NO:4 or SEQ ID NO:6 over the entire length of SEQ ID NO:4 or SEQ ID NO:6, respectively;

(c) comprises the amino acid of SEQ ID NO:4 or SEQ ID NO:6; and (d) is the polypeptide of SEQ ID NO:4 or SEQ ID NO:6; as well as polypeptides encoded by a polynucleotide comprising the sequence contained in SEQ ID NO:3 or SEQ ID NO:5.

The nucleotide sequence of SEQ ID NO:3 or SEQ ID NO:5 and the peptide sequences encoded thereby are derived from EST (Expressed Sequence Tag) sequences. It is recognised by those skilled in the art that there will inevitably be some nucleotide sequence reading errors in EST sequences (see Adams, M. D. et al, *Nature* 377 (supp) 3, 1995). Accordingly, the nucleotide sequence of SEQ ID NO:3 or SEQ ID NO:5 and the peptide sequences encoded therefrom are therefore subject to the same inherent limitations in sequence accuracy. Furthermore, the peptide sequences encoded by SEQ ID NO:3 or SEQ ID NO:5 comprises a region of identity or close homology and/or close structural similarity (for example a conservative amino acid difference) with the closest homologous or structurally similar protein.

The cDNA sequence of FIG. 2 (SEQ ID NO:3) contains an open reading frame encoding a polypeptide of 74 amino acids. The amino acid of sequence of FIG. 2 (SEQ ID NO:4) has about 62% identity (using tfasta) in 14 amino acid residues with Mouse UCP2 (Ricquier, D. et al. Ceremod, CNRS, 1996, gb acc.=U69135). The nucleotide sequence of FIGS. 1 and 1A (SEQ ID NO:1) has about 68% identity (using bestfit) in 16 nucleotide residues with MUCP2 mRNA, complete cds. (Ricquier, D. et al., Ceremod, CNRS, 1996, gb acc.=U69135).

The cDNA sequence of FIG. 3 (SEQ ID NO:5) contains an open reading encoding a polypeptide of 95 amino acids. The amino acid of sequence of FIG. 3 (SEQ ID NO:6) has about 58% identity (using Tfasta) in 14 amino acid residues with Human UCP2 (Fleury, C. et al. Nature Genetics(15), March 1997, genbank accession numberU76367). The nucleotide sequence of FIG. 2 (SEQ ID NO:4) has about 64% identity (using BlastN) in 16 nucleotide residues with Human UCP2 mRNA, complete cds (Fleury, C. et al. Nature Genetics(15), March 1997, genbank accession numberU76367).

One polynucleotide of the present invention encoding HNFCW60 may be obtained using standard cloning and screening, from a cDNA library derived from mRNA in cells of human brain frontal cortex, rhabdomyosarcoma, fetal heart, and skeletal muscle using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). It is noted that two Expressed Sequence Tags (GenBank accession nos; aa192136 and z28895) are represented in parts of HNFCW60. Polynucleotides of the invention can also be obtained from natural sources such as genomic DNA libraries or can be synthesized using well known and commercially available techniques.

The nucleotide sequence encoding HNFCW60 polypeptide of SEQ ID NO:2 may be identical over its entire length to the coding sequence set forth in FIGS. 1 and 1A (SEQ ID NO:1), or may be a degenerate form of this nucleotide sequence encoding the polypeptide of SEQ ID NO:2, or may be highly identical to a nucleotide sequence that encodes the polypeptide of SEQ ID NO:2. Preferably, the polynucleotides of the invention comprise a nucleotide sequence that is highly identical, at least 80% identical, with a nucleotide sequence encoding a HNFCW60 polypeptide, or at least 80% identical with the sequence contained in FIGS. 1 and 1A (SEQ ID NO: 1) encoding HNFCW60 polypeptide, or at least 80% identical to a nucleotide sequence encoding the polypeptide of SEQ ID NO:2.

When the polynucleotides of the invention are used for the recombinant production of HNFCW60 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding HNFCW60 variants comprise the amino acid sequence HNFCW60 polypeptide of FIGS. 1 and 1A (SEQ ID NO:2) in which several, 5–10, 1–5, 1–3, 1–2 or 1 amino acid residues are substituted, deleted or added, in any combination.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Polynucleotides of the invention, which are identical or sufficiently identical to a nucleotide sequence contained in SEQ ID NO:1, may be used as hybridization probes for cDNA and genomic DNA, to isolate full-length cDNAs and genomic clones encoding HNFCW60 polypeptide and to isolate cDNA and genomic clones of other genes that have a high sequence similarity to the HNFCW60 gene. Such hybridization techniques are known to those of skill in the art. Typically these nucleotide sequences are 70% identical, preferably 80% identical, more preferably 90% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding HNFCW60 comprises the steps of screening an appropriate library under stringent hybridization conditions with a labeled probe having the SEQ ID NO: 1 or a fragment thereof; and isolating full-length cDNA and genomic clones containing said polynucleotide sequence. Such hybridization techniques are well known to those of skill in the art. Stringent hybridization conditions are as defined above or alternatively conditions under overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY(1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the HNFCW60 polypeptide is to be expressed for use in screening assays, generally, it is preferred that the polypeptide be produced at the surface of the cell. In this event, the cells may be harvested prior to use in the screening assay. If HNFCW60 polypeptide is secreted into the medium, the medium can be recovered in order to recover and purify the polypeptide; if produced intracellularly, the cells must first be lysed before the polypeptide is recovered.

HNFCW60 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of HNFCW60 polynucleotides for use as diagnostic reagents. Detection of a mutated form of HNFCW60 gene associated with a dysfunction will provide a diagnostic tool that can add to or define a diagnosis of a disease or susceptibility to a disease which results from under-expression, over-expression or altered expression of HNFCW60. Individuals carrying mutations in the HNFCW60 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled HNFCW60 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985)230:1242. Sequence changes at specific locations may also be revealed by nuclease protection assays, such as RNase and S1 protection or the chemical cleavage method. See Cotton et al., *Proc Natl Acad Sci USA* (1985) 85:4397–4401. In another embodiment, an array of oligonucleotides probes comprising HNFCW60 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., *Science*, Vol 274, pp 610–613 (1996)).

The diagnostic assays offer a process for diagnosing or determining a susceptibility to obesity, diabetes, and body weight disorder through detection of mutation in the HNFCW60 gene by the methods described.

In addition, obesity, diabetes, and body weight disorder, can be diagnosed by methods comprising determining from a sample derived from a subject an abnormally decreased or increased level of HNFCW60 polypeptide or HNFCW60 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an HNFCW60 polypeptide, in a sample derived from a host are well-known to those of skill in the art. Such assay methods include radioimmunoassays, competitive-binding assays, Western Blot analysis and ELISA assays.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the HNFCW60 polypeptides. The term "immunospecific" means that the antibodies have substantially greater affinity for the polypeptides of the invention than their affinity for other related polypeptides in the prior art.

Antibodies generated against the HNFCW60 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against HNFCW60 polypeptides may also be employed to treat obesity, diabetes, and body weight disorder, among others.

Vaccines

Another aspect of the invention relates to a method for inducing an immunological response in a mammal which comprises inoculating the mammal with HNFCW60 polypeptide, or a fragment thereof, adequate to produce antibody and/or T cell immune response to protect said animal from obesity, diabetes, and body weight disorder, among others. Yet another aspect of the invention relates to a method of inducing immunological response in a mammal which comprises, delivering HNFCW60 polypeptide via a vector directing expression of HNFCW60 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a HNFCW60 polypeptide wherein the composition comprises a HNFCW60 polypeptide or HNFCW60 gene. The vaccine formulation may further comprise a suitable carrier. Since HNFCW60 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain antioxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The HNFCW60 polypeptide of the present invention may be employed in a screening process for compounds which activate (agonists) or inhibit activation of (antagonists, or otherwise called inhibitors) the HNFCW60 polypeptide of the present invention. Thus, polypeptides of the invention may also be used to assess identify agonist or antagonists from, for example, cells, cell-free preparations, chemical libraries, and natural product mixtures. These agonists or antagonists may be natural substrates, ligands, receptors, etc., as the case may be, of the polypeptide of the present invention; or may be structural or functional mimetics of the polypeptide of the present invention. See Coligan et al., *Current Protocols in Immunology* 1(2):Chapter 5 (1991).

HNFCW60 polypeptides are ubiquitous in the mammalian host and are responsible for many biological functions, including many pathologies. Accordingly, it is desirous to find compounds and drugs which stimulate HNFCW60 polypeptide on the one hand and which can inhibit the function of HNFCW60 polypeptide on the other hand. In general, agonists are employed for therapeutic and prophylactic purposes for such conditions as obesity, diabetes, and body weight disorder. Antagonists may be employed for a variety of therapeutic and prophylactic purposes for such conditions as obesity, diabetes, and body weight disorder.

In general, such screening procedures may involve using appropriate cells which express the HNFCW60 polypeptide or respond to HNFCW60 polypeptide of the present invention. Such cells include cells from mammals, yeast, Drosophila or *E. coli*. Cells which express the HNFCW60 polypeptide (or cell membrane containing the expressed polypeptide) or respond to HNFCW60 polypeptide are then contacted with a test compound to observe binding, or stimulation or inhibition of a functional response. The ability of the cells which were contacted with the candidate compounds is compared with the same cells which were not contacted for HNFCW60 activity.

The assays may simply test binding of a candidate compound wherein adherence to the cells bearing the HNFCW60 polypeptide is detected by means of a label directly or indirectly associated with the candidate compound or in an assay involving competition with a labeled competitor. Further, these assays may test whether the candidate compound results in a signal generated by activation of the HNFCW60 polypeptide, using detection systems appropriate to the cells bearing the HNFCW60 polypeptide. Inhibitors of activation are generally assayed in the presence of a known agonist and the effect on activation by the agonist by the presence of the candidate compound is observed. Standard methods for conducting such screening assays are well understood in the art.

Examples of potential HNFCW60 polypeptide antagonists include antibodies or, in some cases, oligonucleotides or proteins which are closely related to the ligands, substrates, receptors, etc., as the case may be, of the HNFCW60 polypeptide, e.g., a fragment of the ligands, substrates, receptors, or small molecules which bind to the polypetide of the present invention but do not elicit a response, so that the activity of the polypeptide is prevented.

Prophylactic and Therapeutic Methods

This invention provides methods of treating an abnormal conditions related to both an excess of and insufficient amounts of HNFCW60 polypeptide activity.

If the activity of HNFCW60 polypeptide is in excess, several approaches are available. One approach comprises administering to a subject an inhibitor compound (antagonist) as hereinabove described along with a pharmaceutically acceptable carrier in an amount effective to inhibit activation by blocking binding of ligands to the HNFCW60 polypeptide, or by inhibiting a second signal, and thereby alleviating the abnormal condition.

In another approach, soluble forms of HNFCW60 polypeptides still capable of binding the ligand in competition with endogenous HNFCW60 polypeptide may be administered. Typical embodiments of such competitors comprise fragments of the HNFCW60 polypeptide.

In still another approach, expression of the gene encoding endogenous HNFCW60 polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an underexpression of HNFCW60 and its activity, several approaches are also available. One approach comprises administering to a subject a therapeutically effective amount of a compound which activates HNFCW60 polypeptide, i.e., an agonist as described above, in combination with a pharmaceutically acceptable carrier, to thereby alleviate the abnormal condition. Alternatively, gene therapy may be employed to effect the endogenous production of HNFCW60 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996).

Formulation and Administration

Peptides, such as the soluble form of HNFCW60 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Definitions

The following definitions are provided to facilitate understanding of certain terms used frequently hereinbefore.

"HNFCW60 activity or HNFCW60 polypeptide activity" or "biological activity of the HNFCW60 or HNFCW60 polypeptide" refers to the metabolic or physiologic function of said HNFCW60 including similar activities or improved activities or these activities with decreased undesirable side-effects. Also included are antigenic and immunogenic activities of said HNFCW60.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215: 403–410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403–410 (1990). The well known Smith Waterman algorithm may also be used to determine identity.

Preferred parameters for polypeptide sequence comparison include the following:
1) Algorithm: Needleman and Wunsch, J. Mol Biol. 48: 443–453 (1970)

Comparison matrix: BLOSSUM62 from Hentikoff and Hentikoff, Proc. Natl. Acad. Sci. USA. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for polypeptide comparisons (along with no penalty for end gaps).

Preferred parameters for polynucleotide comparison include the following:
1) Algorithm: Needleman and Wunsch, J. Mol Biol. 48: 443–453 (1970)

Comparison matrix: matches=+10, mismatch=0

Gap Penalty: 50

Gap Length Penalty: 3

A program useful with these parameters is publicly available as the "gap" program from Genetics Computer Group, Madison Wis. The aforementioned parameters are the default parameters for polynucleotide comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity(divided by 100) and subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%, etc., and wherein any non-integer product of xn and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity(divided by 100) and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

EXAMPLES

1. Sequence

Uncoupling protein 3' (UCP3) sequence was determined using the technique of 5' RACE (rapid amplification of cDNA ends) using Marathon-Ready™ Skeletal muscle cDNA (Clontech Laboratories Inc) using the manufacturers recommended protocol with nested primers designed from overlapping 3' EST. A 1000 bp 5' RACE fragment was subcloned into plasmid pGEM T (Promega) and double strand sequenced. The sequence was found to extend through the 5' end of the gene and a further 198 bp into the 5'.

Sequence generated from the 5'RACE fragment was aligned with the sequence from NCBI EST aa192136 to generate an electronic full length UCP3 sequence.

Primers were designed in the 5' and 3' UTR regions of the electronic sequence and used to PCR the full UCP3 gene from Marathon Ready™ Skeletal Muscle cDNA using a proof reading enzyme (pfu polymerase-Stratagene) according to the manufacturers recommended protocol.

The final product was subcloned into the vector pTAR-GET (Promega) and the full sequence confirmed by double strand sequencing using multiple primers to generate sequence overlaps.

2. Tissue Distribution i) Northern Analysis

A digoxygenin (DIG)-labelled cDNA probe was synthesised by PCR incorporation of DIG-dUTP (Boehringer Mannheim) using primers designed using HHFCW603:

UCP3F
5'-GGT GGT GAC CTA CGA CAT CCT CAA GG-3'
UCP3R
5'-GGC CTG CAG GTG AGT TCA TAT ACC G-3'

The labelled PCR product was purified using Wizard PCR prep™ kit (Promega) and hybridised with commercially available human multiple tissue northern blots (MTN-I, -II and -III; Clontech) containing 2 ug polyA$^+$ mRNA for the following tissues: heart, brain, placenta, lung, liver, skeletal muscle, kidney, pancreas, spleen, thymus, prostate, testis, ovary, small intestine, colon, peripheral blood leukocyte, stomach, thyroid, spinal cord, lymph node, trachea, adrenal gland and bone marrow.

Hybridisation was performed overnight at 50° C. using EasyHyb™ (Boehringer Mannheim) solution. Chemiluminescent detection was performed as described in Clapham et al., 1997, Int. J. Obesity, 21: 179–183). Of all the tissues tested by this method a strong signal indicating a transcript size of 2.0 kb was evident in skeletal muscle with some presence detectable in bone marrow.

ii) Southern Analysis

Genomic analysis of the DIG-UCP3 cDNA probe was performed using a commercial Zooblot™ (Clontech) and overnight hybridisation at 40° C. in EasyHyb™. Chemiluminescent detection was performed as before. UCP3 was present in all mammalian genomic DNA tested (human, monkey, rat, mouse, dog, cow and rabbit) but was absent from chicken and yeast genomic DNA.

iii) RT-PCR

Using primers UCP3F and UCP3R, PCR analysis was performed using human cDNA from white adipose tissue, liver, skeletal muscle, pancreas, heart, bone marrow, kidney, lung, prostate, whole brain and testis cDNA.

The presence of UCP3 was confirmed in skeletal muscle and bone marrow but additional, faint, signals were detected in pancreas, kidney and brain cDNAs. Unlike UCP2 (Fleury, C. et al. Nature Genetics(15), March 1997, gb acc.= U76367), UCP3 was absent from liver and white adipose tissue.

FIG. 1. Nucleotide and translated Amino Acid sequence from HNFCW60 (SEQ ID NOS: 1 and 2, respectively.)

| | | |
|---|---|---|
| 1 | CGCCCGGGCAGGTCAAGGTCAAGGAGGGGCCATCCAATTCCCTGCTGCCACCTCC | 48 |
| 49 | TGGGATGGAGCCCTAGGGAGCCCCTGTGCTGCCCCTGCCGTGGCAGGA | 96 |
| 97 | CTCACAGCCCCACCGCTGCACTGAAGCCCAGGGCTGTGGAGCAGCCTC | 144 |
| 145 | TCTCCTTGGACCTCCTCTCGGCCCTAAAGGGACTGGGCAGAGCCTTCC | 192 |

-continued

```
 193 AGGACTATGGTTGGACTGAAGCCTTCAGACGTGCCTCCCACCATGCT            240
       M  V  G  L  K  P  S  D  V  P  P  T  M  A

241 GTGAAGTTCCTGGGGGCAGGCACAGCAGCCTGTTTTGCTGACCTCGTT            288
      V  K  F  L  G  A  G  T  A  A  C  F  A  D  L  V

289 ACCTTTCCACTGGACACAGCCAAGGTCCGCCTGCAGATCCAGGGGGAG            336
      T  F  P  L  D  T  A  K  V  R  L  Q  I  Q  G  E

337 AACCAGGCGGTCCAGACGGCCCGGCTCGTGCAGTACCGTGGCGTGCTG            384
      N  Q  A  V  Q  T  A  R  L  V  Q  Y  R  G  V  L

385 GGCACCATCCTGACCATGGTGCGGACTGAGGGTCCCTGCAGCCCCTAC            432
      G  T  I  L  T  M  V  R  T  E  G  P  C  S  P  Y

433 AATGGGCTGGTGGCCGGCCTGCAGCGCCAGATGAGCTTCGCCTCCATC            480
      N  G  L  V  A  G  L  Q  R  Q  M  S  F  A  S  I

481 CGCATCGGCCTCTACGACTCCGTCAAGCAGGTGTACACCCCCAAAGGC            528
      R  I  G  L  Y  D  S  V  K  Q  V  Y  T  P  K  G

529 GCGGACAACTCCAGCCTCACTACCCGGATTTTGGCCGGCTGCACCACA            576
      A  D  N  S  S  L  T  T  R  I  L  A  G  C  T  T

577 GGAGCCATGGCGGTGACCTGTGCCCAGCCCACAGATGTGGTGAAGGTC            624
      G  A  M  A  V  T  C  A  Q  P  T  D  V  V  K  V

625 CGATTTCAGGCCAGCATACACCTCGGGCCATCCAGGAGCGACAGAAAA            672
      R  F  Q  A  S  I  H  L  G  P  S  R  S  D  R  K

673 TACAGCGGGACTATGGACGCCTACAGAACCATCGCCAGGGAGGAAGGA            720
      Y  S  G  T  M  D  A  Y  R  T  I  A  R  E  E  G

721 GTCAGGGGCCTGTGGAAAGGAACTTTGCCCAACATCATGAGGAATGCT            768
      V  R  G  L  W  K  G  T  L  P  N  I  M  R  N  A

769 ATCGTCAACTGTGCTGAGGTGGTGACCTACGACATCCTCAAGGAGAAG            816
      I  V  N  C  A  E  V  V  T  Y  D  I  L  K  E  K

817 CTGCTGGACTACCACCTGCTCACTGACAACTTCCCCTGCCACTTTGTC            864
      L  L  D  Y  H  L  L  T  D  N  F  P  C  H  F

865 TCTGCCTTTGGAGCCGGCTTCTGTGCCACAGTGGTGGCCTCCCCGGTG            912
      S  A  F  G  A  G  F  C  A  T  V  V  A  S  P  V

913 GACGTGGTGAAGACCCGGTATATGAACTCACCTCCAGGCCAGTACTTC            960
      D  V  V  K  T  R  Y  M  N  S  P  P  G  Q  Y  F

961 AGCCCCCTCGACTGTATGATAAAGATGGTGGCCCAGGAGGGCCCCACA           1008
      S  P  L  D  C  M  I  K  M  V  A  Q  E  G  P  T

1009 GCCTTCTACAAGGGATTTACACCCTCCTTTTTGCGTTTGGGATCCTGG           1056
      A  F  Y  K  G  F  T  P  S  F  L  R  L  G  S  W

1057 AACGTGGTGATGTTCGTAACCTATGAGCAGCTGAAACGGGCCCTGATG           1104
      N  V  V  M  F  V  T  Y  E  Q  L  K  R  A  L  M

1105 AAAGTCCAGATGTTACGGGAATCACCGTTTTGAACAAGACAAGAAGGC           1152
      K  V  Q  M  L  R  E  S  F  F  *

1153 CACTGGTAGCTAACGTGTCCGAAACCAGTTAAGAATGGAAG                  1193
```

FIG. 2. Nucleotide and Amino Acid sequence from a HNFCW60
(SEQ ID NOS: 3 and 4, respectively.)

```
  1 CTGGACTACCACCTGCTCACTGACAACTTCCCCTGCCACTTTGTCTCTGCCTTTGGAGCC     60
     L  D  Y  H  L  L  T  D  N  F  F  C  H  F  V  S  A  F  G  A

61 GGCTTCTGTGCCACAGTGGTGGCCTCCCCGGTGGACGTGGTGAAGACCCGGTATATGAAC    120
     G  F  C  A  T  V  V  A  S  F  V  D  V  V  K  T  Y  M  N

121 TCACCTCCAGGCCAGTACTTCAGCCCCCTCGACTGTATGATAAAGATGGTGGCCCAGGAG    180
     S  F  F  G  Q  Y  F  S  P  L  D  C  M  I  K  M  V  A  Q  E

181 GGCCCACAGgCCTTCTACAAGGGGTGAGCCTCCTCCTGCCTCC                    223
     G  F  Q  A  F  Y  K  G  *  A  S  S  C  L
```

FIG. 3. Nucleotide and partially translated Amino Acid sequence from HNFCW60 (SEQ ID NOS: 5 and 6, respectively.)

SEQ ID NO: 5

```
  1 AAGAGCTCAX XXTXTATGTT GAATXATTTT TTTTXXTGGC TGCAGCTGGG
 51 TCTCCAGGAA GCXTATTTAA ATTTXAACAG CTATTGCAGA TCACCCTCCA
101 AATGTGGCCA AATGAACACA AGTGGGCCTC TXTTTXCTXT XTXTCTXAGG
151 AXAACATGGA TAATCTGAGA XTTGTTAACC CTAGAAAGGA AAATXTGGAA
201 TCTXCTCAGC TGGGGTGGGA TCCTCTGGCT GAGACCATTG GAATGGGGCA
251 CTATGGCCCC AAAACTGGGG CCTGTGGCCT TGCAGCCAGG GCATCCATTT
301 TTXCCATTTC CCATTCCTCC CTCCCCAYCS ATWKGRMAKS MMKSMSTCAS
351 SGGCYTSYKG AACAGGAACT TTSCCCAACA TCATGXAGGA ATGCTATCGT
401 CAACTGTSCT GAGGTGGTGA CCTACGACAT CCTCAAGGAG AAGCTGCTGG
451 ACTAYCACCT GCTCACTGAC AACTTCCCCT GCCACTTTGT CTCTGCCTTT
501 GGAGCCGGCT TCTGTGCCAC AGTGGTGGCM TCCCCGGTGG AQGTGGTGAA
551 GACCCGGTAT ATGAACTCAC CTCCAGGCCA GTACTTCAGC CCCCTCGACT
601 GTATGATAAA GATGGTGGCC CAGGAGSGCC ACACAGCCTT CTACAAGGGA
651 KTKASMCTCC TCCTKYYTSC AGYWYKSSMT CCYAGAGAAC AGKGGCTKMT
701 GTTCKTWWCS WATGAGCAGC TGAAACGGGC CCTGATGAAA GTCCAGATGT
751 TACGGGAATC ACCGTTTTGA ACAAGACAAG AAGGCCACTG GTAGCTAACG
801 TGTCCGAAAC CAGTTAAGAA TGGAAGAAAA CGGTGCATCC ACGXACACAT
851 GGACACAGAC CCACACATXT T
```

SEQ ID NO: 6
Sequence numbers refer to equivalent positions of nucleotides in HNFCW60

```
375 GTXPNIMRNAIVNCXEVVTYDILKEKLLDYHLLTDNFPCHFVSAFGAGFCATVVASPVDV   524
525 VKTRYMNSPPGQYFSPLDCMIKMVAQEXHTAFYK                              650
```

---

What is claimed is:

1. An isolated polynucleotide comprising the polynucleotide sequence set forth in SEQ ID NO: 1.

2. The isolated polynucleotide of claim 1 consisting of the polynucleotide sequence of SEQ ID NO:1.

3. An isolated polynucleotide which is fully complementary to
   (a) a nucleotide sequence comprising the polynucleotide sequence of SEQ ID NO:1; or
   (b) a nucleotide sequence consisting of the polynucleotide sequence of SEQ ID NO:1.

4. An isolated polynucleotide comprising the polynucleotide sequence of SEQ ID NO:3.

5. The isolated polynucleotide of claim 4 consisting of the polynucleotide sequence of SEQ ID NO:3.

6. An isolated polynucleotide encoding the polypeptide sequence of SEQ ID NO:6.

7. An isolated polynucleotide comprising the polynucleotide sequence set forth in SEQ ID NO: 5.

8. The isolated polynucleotide of claim 7 consisting of the polynucleotide sequence set forth in SEQ ID NO:5.

9. An isolated polynucleotide which is fully complementary to
   (a) a nucleotide sequence comprising the polynucleotide sequence of SEQ ID NO:3;
   (b) a nucleotide sequence consisting of the polynucleotide sequence of SEQ ID NO:3;
   (c) a nucleotide sequence comprising the polynucleotide sequence of SEQ ID NO:5; or
   (d) a nucleotide sequence consisting of the polynucleotide sequence of SEQ ID NO:5.

10. An expression system comprising a polynucleotide encoding SEQ ID NO:2, wherein said expression system is capable of producing a polypeptide comprising the amino acid sequence of SEQ ID NO:2 when said expression system is present in a compatible host cell.

11. A host cell comprising the expression system of claim 10 or a membrane thereof expressing a polypeptide comprising the amino acid sequence of SEQ ID NO:2.

12. A process for producing a polypeptide comprising the amino acid sequence of SEQ ID NO:2 comprising culturing a host cell of claim 11 under conditions sufficient for the production of said polypeptide and recovering the polypeptide from the culture medium.

* * * * *

SEQUENCE LISTING

<160> NUMBER OF SEQ IDS NOS: 6

<210> SEQ ID NO 1
<211> LENGTH: 1192
<212> TYPE: DNA
<213> ORGANISM: HOMO SAPIEN

<400> SEQUENCE: 1

```
cgcccgggca ggtcaaggag gggccatcca atccctgctg ccacctcctg ggatggagcc    60
ctagggagcc cctgtgctgc ccctgccgtg gcaggactca cagccccacc gctgcactga   120
agcccagggc tgtggagcag cctctctcct tggacctcct ctcggcccta aagggactgg   180
gcagagcctt ccaggactat ggttggactg aagccttcag acgtgcctcc caccatggct   240
gtgaagttcc tggggcagg cacagcagcc tgttttgctg acctcgttac ctttccactg   300
gacacagcca aggtccgcct gcagatccag ggggagaacc aggcggtcca gacggcccgg   360
ctcgtgcagt accgtggcgt gctgggcacc atcctgacca tggtgcggac tgagggtccc   420
```

```
tgcagccct acaatgggct ggtggccggc ctgcagcgcc agatgagctt cgcctccatc    480
cgcatcggcc tctacgactc cgtcaagcag gtgtacaccc ccaaaggcgc ggacaactcc    540
agcctcacta cccggatttt ggccggctgc accacaggag ccatggcggt gacctgtgcc    600
cagcccacag atgtggtgaa ggtccgattt caggccagca tacacctcgg ccatccaggg   660
agcgacagaa aatacagcgg gactatggac gcctacagaa ccatcgccag ggaggaagga   720
gtcaggggcc tgtggaaagg aactttgccc aacatcatga ggaatgctat cgtcaactgt   780
gctgaggtgg tgacctacga catcctcaag gagaagctgc tggactacca cctgctcact   840
gacaacttcc cctgccactt tgtctctgcc tttggagccg gcttctgtgc cacagtggtg   900
gcctccccgg tggacgtggt gaagacccgg tatatgaact cacctccagg ccagtacttc   960
agccccctcg actgtatgat aaagatggtg gcccaggagg gccccacagc cttctacaag  1020
ggatttacac cctcctttttt gcgtttggga tcctggaacg tggtgatgtt cgtaacctat  1080
gagcagctga aacgggccct gatgaaagtc cagatgttac gggaatcacc gttttgaaca  1140
agacaagaag gccactggta gctaacgtgt ccgaaaccag ttaagaatgg aa           1192
```

<210> SEQ ID NO 2
<211> LENGTH: 312
<212> TYPE: PRT
<213> ORGANISM: HOMO SAPIEN

<400> SEQUENCE: 2

```
Met Val Gly Leu Lys Pro Ser Asp Val Pro Thr Met Ala Val Lys
 1               5                  10                  15

Phe Leu Gly Ala Gly Thr Ala Ala Cys Phe Ala Asp Leu Val Thr Phe
                20                  25                  30

Pro Leu Asp Thr Ala Lys Val Arg Leu Gln Ile Gln Gly Glu Asn Gln
             35                  40                  45

Ala Val Gln Thr Ala Arg Leu Val Gln Tyr Arg Gly Val Leu Gly Thr
         50                  55                  60

Ile Leu Thr Met Val Arg Thr Glu Gly Pro Cys Ser Pro Tyr Asn Gly
 65                  70                  75                  80

Leu Val Ala Gly Leu Gln Arg Gln Met Ser Phe Ala Ser Ile Arg Ile
                 85                  90                  95

Gly Leu Tyr Asp Ser Val Lys Gln Val Tyr Thr Pro Lys Gly Ala Asp
                100                 105                 110

Asn Ser Ser Leu Thr Thr Arg Ile Leu Ala Gly Cys Thr Thr Gly Ala
            115                 120                 125

Met Ala Val Thr Cys Ala Gln Pro Thr Asp Val Val Lys Val Arg Phe
        130                 135                 140

Gln Ala Ser Ile His Leu Gly Pro Ser Arg Ser Asp Arg Lys Tyr Ser
145                 150                 155                 160

Gly Thr Met Asp Ala Tyr Arg Thr Ile Ala Arg Glu Glu Gly Val Arg
                165                 170                 175

Gly Leu Trp Lys Gly Thr Leu Pro Asn Ile Met Arg Asn Ala Ile Val
                180                 185                 190

Asn Cys Ala Glu Val Val Thr Tyr Asp Ile Leu Lys Glu Lys Leu Leu
            195                 200                 205

Asp Tyr His Leu Leu Thr Asp Asn Phe Pro Cys His Phe Val Ser Ala
        210                 215                 220

Phe Gly Ala Gly Phe Cys Ala Thr Val Val Ala Ser Pro Val Asp Val
225                 230                 235                 240
```

```
Val Lys Thr Arg Tyr Met Asn Ser Pro Pro Gly Gln Tyr Phe Ser Pro
            245                 250                 255

Leu Asp Cys Met Ile Lys Met Val Ala Gln Glu Gly Pro Thr Ala Phe
        260                 265                 270

Tyr Lys Gly Phe Thr Pro Ser Phe Leu Arg Leu Gly Ser Trp Asn Val
    275                 280                 285

Val Met Phe Val Thr Tyr Glu Gln Leu Lys Arg Ala Leu Met Lys Val
    290                 295                 300

Gln Met Leu Arg Glu Ser Pro Phe
305                 310
```

<210> SEQ ID NO 3
<211> LENGTH: 222
<212> TYPE: DNA
<213> ORGANISM: HOMO SAPIEN

<400> SEQUENCE: 3

```
ctggactacc acctgctcac tgacaacttc ccctgccact tgtctctgc ctttggagcc      60
ggcttctgtg ccacagtggt ggcctccccg gtggacgtgg tgaagacccg gtatatgaac   120
tcacctccag gccagtactt cagccccctc gactgtatga aaagatggt ggcccaggag   180
ggcccacagg ccttctacaa ggggtgagcc tcctcctgcc tc                      222
```

<210> SEQ ID NO 4
<211> LENGTH: 74
<212> TYPE: PRT
<213> ORGANISM: HOMO SAPIEN
<220> FEATURE:
<221> NAME/KEY: unsure
<222> LOCATION: (69)

<400> SEQUENCE: 4

```
Leu Asp Tyr His Leu Leu Thr Asp Asn Phe Pro Cys His Phe Val Ser
 1               5                  10                  15

Ala Phe Gly Ala Gly Phe Cys Ala Thr Val Val Ala Ser Pro Val Asp
            20                  25                  30

Val Val Lys Thr Arg Tyr Met Asn Ser Pro Pro Gly Gln Tyr Phe Ser
        35                  40                  45

Pro Leu Asp Cys Met Ile Lys Met Val Ala Gln Glu Gly Pro Gln Ala
    50                  55                  60

Phe Tyr Lys Gly Xaa Ala Ser Ser Cys Leu
65                  70
```

<210> SEQ ID NO 5
<211> LENGTH: 847
<212> TYPE: DNA
<213> ORGANISM: HOMO SAPIEN
<220> FEATURE:
<221> NAME/KEY: unsure
<222> LOCATION: (310)(313)(314)(316)(317)(319)(320)(321)(322)(323)
<222> LOCATION: (324)(325)(326)(330) (331)(335)(337)(338)(339)(339)
<222> LOCATION: (353)(387)(434)(509)(630)(632)(634)(536)(644)(645)
<222> LOCATION: (646)(648)(651)(652)(653)(654)(655)(656)(657)(658)
<222> LOCATION: (662)(672)(677)(678)(680)(684)(686)(687)(689)(690)

<400> SEQUENCE: 5

```
aagagctcat tatgttgaat attttttttt ggctgcagct gggtctccag gaagctattt      60
aaatttaaca gctattgcag atcaccctcc aaatgtggcc aaatgaacac aagtgggcct   120
cttttctttt ctaggaaaca tggataatct gagattgtta accctagaaa ggaaaattgg   180
aatctctcag ctggggtggg atcctctggc tgagaccatt ggaatggggc actatggccc   240
```

-continued

```
caaaactggg gcctgtggcc ttgcagccag ggcatccatt tttccatttc ccattcctcc      300
ctccccaycs atwkgrmaks mmksmstcas sggcytsykg aacaggaact ttscccaaca      360
tcatgaggaa tgctatcgtc aactgtsctg aggtggtgac ctacgacatc ctcaaggaga      420
agctgctgga ctaycacctg ctcactgaca acttcccctg ccactttgtc tctgcctttg      480
gagccggctt ctgtgccaca gtggtggcmt ccccggtgga cgtggtgaag acccggtata      540
tgaactcacc tccaggccag tacttcagcc ccctcgactg tatgataaag atggtggccc      600
aggagsgcca cacagccttc tacaagggak tkasmctcct cctkyytsca gywykssmtc      660
cyagagaaca gkggctkmtg ttcktwwcsw atgagcagct gaaacgggcc ctgatgaaag      720
tccagatgtt acgggaatca ccgttttgaa caagacaaga aggccactgg tagctaacgt      780
gtccgaaacc agttaagaat ggaagaaaac ggtgcatcca cgacacatgg acacagaccc      840
acacatt                                                                847
```

<210> SEQ ID NO 6
<211> LENGTH: 95
<212> TYPE: PRT
<213> ORGANISM: HOMO SAPIEN
<220> FEATURE:
<221> NAME/KEY: unsure
<222> LOCATION: (3)(15)(88)

<400> SEQUENCE: 6

Gly Thr Xaa Pro Asn Ile Met Arg Asn Ala Ile Val Asn Cys Xaa Glu
 1               5                  10                  15

Val Val Thr Tyr Asp Ile Leu Lys Glu Lys Leu Leu Asp Tyr His Leu
            20                  25                  30

Leu Thr Asp Asn Phe Pro Cys His Phe Val Ser Ala Phe Gly Ala Gly
        35                  40                  45

Phe Cys Ala Thr Val Val Ala Ser Pro Val Asp Val Val Lys Thr Arg
    50                  55                  60

Tyr Met Asn Ser Pro Pro Gly Gln Tyr Phe Ser Pro Leu Asp Cys Met
65                  70                  75                  80

Ile Lys Met Val Ala Gln Glu Xaa His Thr Ala Phe Tyr Lys Gly
                85                  90                  95